(12) United States Patent
Gottesman (10) Patent No.: US 11,624,081 B2
(45) Date of Patent: Apr. 11, 2023

(54) MODIFIED BACTERIAL PROTEIN EXPRESSION SYSTEM

(71) Applicant: THE TRUSTESS OF COLUMBIA UNIVERSITY IN THE CITY OF NEW YORK, New York, NY (US)

(72) Inventor: Maxwell Gottesman, New York, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 344 days.

(21) Appl. No.: 16/886,156

(22) Filed: May 28, 2020

(65) Prior Publication Data

US 2020/0362383 A1    Nov. 19, 2020

Related U.S. Application Data

(62) Division of application No. 15/764,070, filed as application No. PCT/US2016/054130 on Sep. 28, 2016, now Pat. No. 10,745,730.

(60) Provisional application No. 62/233,507, filed on Sep. 28, 2015.

(51) Int. Cl.
| | |
|---|---|
| *C12N 9/52* | (2006.01) |
| *C12P 21/02* | (2006.01) |
| *C07K 14/245* | (2006.01) |
| *C12N 15/10* | (2006.01) |
| *C12N 15/70* | (2006.01) |

(52) U.S. Cl.
CPC ............ *C12P 21/02* (2013.01); *C07K 14/245* (2013.01); *C12N 9/52* (2013.01); *C12N 15/102* (2013.01); *C12N 15/70* (2013.01)

(58) Field of Classification Search
CPC .......... C12N 15/74; C12N 15/00; C12N 9/16; C12N 9/6424; C12N 15/65; C12Y 301/00; C12Y 207/01011
USPC ........................ 435/252.31, 69.7, 196, 320.1
See application file for complete search history.

(56) References Cited

U.S. PATENT DOCUMENTS

| | | | |
|---|---|---|---|
| 8,535,909 B2 | 9/2013 | Woldike et al. | |
| 2014/0322388 A1 | 10/2014 | Liu | |

FOREIGN PATENT DOCUMENTS

| | | |
|---|---|---|
| WO | 2014089375 | 6/2014 |
| WO | 2014138679 | 9/2014 |
| WO | 201464869 | 10/2014 |

OTHER PUBLICATIONS

Studier WF, Protein production by auto-induction in high density shaking cultures. Protein Expression and Purification, 2015, vol. 41, Issue 1, pp. 207-234.
F. William Studier, Stable expression clones and auto-induction for protein production in *E. coli*, Methods in Molecular Biology, vol. 1091, pp. 17-32, 2014.
International Search Report and Written Opinion dated Mar. 22, 2017 corresponding to International Application No. PCT/US2016/054130; 13 pages.
Novagen pET System Manual 11th Edition, 63 pages, 2011.
Julien Ratelade, et al., Production of recombinant proteins in the ion-deficient BL21 (DE3) strain of *Escherichia coli* in the absence of DnaK chaperone, Applied and Environmental Microbiology, Jun. 2009, pp. 3803-3807 (2009).
Garcia-Fruitos, et al., Divergent genetic control of protein solubility and conformational quality in *Escherichia coli*, J Mol Biol, Nov. 1, 20076;374(1): 195-205, Epub Sep. 8, 2007 (2007).
McGinness, et al., Engineering controllable protein degradation, Mol Cell, Jun. 9, 2006, 22(5):701-7; p. 704, Figure 3, and its legend, p. 706, col. 1.
Rosano et al., Recombinant protein expression in *Escherichia coli*: advances and challenges, Front Microbiol, Apr. 17, 2014, vol. 5, Article 172, pp. 1-17; p. 5, col. 2.

*Primary Examiner* — Robert B Mondesi
*Assistant Examiner* — Mohammad Y Meah (57) ABSTRACT

The present disclosure provides host cells for reliable, high yield recombinant protein production, including unstable proteins. The present host cell (e.g., a bacterial cell) is deficient in at least one protease (or a subunit of a protease) such as Clp or ClpP. The host cell may also contain an expression vector that encodes a protein or polypeptide for overexpression.

16 Claims, 3 Drawing Sheets

Specification includes a Sequence Listing.

MODIFIED BACTERIAL PROTEIN EXPRESSION SYSTEM

CROSS REFERENCE TO RELATED APPLICATION

This is a divisional application under 35 U.S.C. § 121 of U.S. Ser. No. 15/764,070, filed Mar. 28, 2018, which was the National Stage application under 35 U.S.C. § 371 of International Application No. PCT/US2016/54130, filed Sep. 28, 2016, which claims benefit under 35 U.S.C. § 119(e) to U.S. Provisional Application No. 62/233,507, filed Sep. 28, 2015, which U.S. Provisional Application is incorporated by reference herein in its entirety.

GOVERNMENT LICENSE RIGHTS

This invention was made with government support under the National Institutes of Health (NIH) Grant No. GM037219. The government may have certain rights in the invention.

FIELD OF THE INVENTION

The present disclosure relates to methods and systems for expressing/overexpressing proteins in prokaryotic cells. In particular, the present disclosure relates to bacteria that have high levels of protein expression due to disrupted proteases.

BACKGROUND INFORMATION

Commonly used protein expression systems include those derived from bacteria, yeast, baculovirus/insect cells, and mammalian cells. Bacterial expression systems, such as *Escherichia coli*, have the advantage of fast growth kinetics, easily achieving high cell density cultures, and fast and easy transformation with exogenous DNA. However, current bacterial expression systems often result in low protein yields or unstable proteins.

Energy-dependent degradation in *Escherichia coli* is carried out by a number of ATP-dependent proteases, including Lon, FtsH, and different Clp proteases. Gottesman S., (1996) Proteases and their targets in *Escherichia coli*. Annu. Rev. Genet. 30:465-506. The Clp proteases are composed of two different multimeric components. The smaller subunit is a peptidase, either ClpP or ClpQ (HslV). Maurizi et al., (1990) Sequence and structure of ClpP, the proteolytic component of the ATP-dependent Clp protease of *Escherichia coli*. J. Biol. Chem. 265:12536-12545. Missiakas et al., Identification and characterization of HslV HslU (ClpQ ClpY) proteins involved in overall proteolysis of misfolded proteins in *Escherichia coli*. EMBO J. 15:6899-6909. The larger subunit is an ATPase, ClpA, ClpX, or ClpY (also called HslU). Katayama-Fujimura et all, (1987) A multiple-component ATP-dependent protease from *Escherichia coli*. J. Biol. Chem. 262:4477-4485. Gottesman et al., (1993) ClpX, an alternative subunit for the ATP-dependent Clp protease of *Escherichia coli*. J. Biol. Chem. 268:22618-22626. Rohrwild et al., (1996) HslV-HslU: a novel ATP-dependent protease complex in *Escherichia coli* related to the eukaryotic proteasome. Proc. Natl. Acad. Sci. USA 93:5808-5813. Wu, et al., Redundant In Vivo Proteolytic Activities of *Escherichia coli* Lon and the ClpYQ (HslUV) Protease, J. Bacteriol. June 1999 vol. 181 no. 12 3681-3687.

Either ClpA or ClpX can associate with ClpP to form an ATP-dependent protease (ClpAP or ClpXP). ClpY associates with ClpQ to form an active, energy-dependent protease. While ClpY and ClpX show significant sequence similarity to each other and to ClpA, ClpP and ClpQ(HslV) are not related at the sequence level. ClpP is a serine protease, found in many prokaryotes and in the organelles of many eukaryotes; ClpQ has a catalytic amino-terminal threonine residue and shows sequence similarity to the eukaryotic proteasome P subunit. Seemuller et al., (1995) Proteasome from *Thermoplasma acidophilum*: a threonine protease. Science, 268:579-582.

Like other parental *E. coli* B strains, BL21 cells are deficient in the Lon protease, which degrades many foreign proteins. Gottesman S. (1996) Proteases and their targets in *Escherichia coli*. Annu. Rev. Genet. 30 465-506. Another gene missing from the genome of the ancestors of BL21 is the outer membrane protease OmpT, whose function is to degrade extracellular proteins. In the BL21(DE3) strain, the λDE3 prophage was inserted in the chromosome of BL21 and contains the T7 RNAP gene under the lacUV5 promoter. The BL21(DE3) and its derivatives, as well as the K-12 lineage are widely used for protein expression. Rosano et al., Recombinant protein expression in *Escherichia coli*: advances and challenges, Front Microbiol. 2014, 5:172.

The present disclosure relates to bacteria that have high levels of protein expression due to disruption of at least one protease. The present disclosure also provides for a method to improve the yield of expressed recombinant proteins, including unstable proteins.

SUMMARY

The present disclosure provides for an engineered bacterium comprising at least one deficient protease. The protease may be Clp, ClpP, ClpQ (HslV), ClpAP, ClpXP, ClpAXP, ClpYQ, ClpA, ClpX, ClpY (HslU), or combinations thereof. The bacterium may overexpress a polypeptide (or protein) at a level which is at least about 2 fold, at least about 3 fold, at least about 4 fold, at least about 5 fold, at least about 6 fold, at least about 8 fold, at least about 10 fold, at least about 12 fold, at least about 14 fold, at least about 15 fold, at least about 16 fold, at least about 18 fold, at least about 19 fold, at least about 20 fold, at least about 25 fold, or at least about 30 fold, of the level of the polypeptide (or protein) produced by a bacterium not engineered with the deficient protease.

The present disclosure also provides for an engineered bacterium comprising a total or partial deletion of at least one gene encoding a protease. The protease may be Clp, ClpP, ClpQ (HslV), ClpAP, ClpXP, ClpAXP, ClpYQ, ClpA, ClpX, ClpY (HslU), or combinations thereof.

Also encompassed by the present disclosure is a method for overexpressing a polypeptide (or protein). The method may comprise the following steps: (a) culturing the present engineered bacterium to produce the polypeptide (or protein); and (b) isolating the polypeptide (or protein).

The present disclosure also provides for a method for overexpressing a polypeptide (or protein) in bacteria, the method comprising the steps of: (a) transforming the present engineered bacterium with a nucleic acid sequence encoding the polypeptide (or protein); (b) culturing the bacterium to produce the polypeptide (or protein); and (c) isolating the polypeptide (or protein).

The present disclosure also provides for a method for expressing a polypeptide (or protein) in bacteria, the method comprising the steps of: (a) engineering a bacterial cell to decrease level and/or activity of at least one protease, wherein the protease is Clp, ClpP, ClpQ (HslV), ClpAP, ClpXP, ClpAXP, ClpYQ, ClpA, ClpX, ClpY (HslU), or combinations thereof; (b) transforming the engineered bacterial cell with a nucleic acid sequence encoding the polypeptide; (c) culturing the bacterium to produce the polypeptide; and (d) isolating the polypeptide.

The engineered bacterium may have deficient ClpP. The engineered bacterium may have a total or partial deletion of a gene encoding ClpP.

The engineered bacterium may further comprise deficient Lon, OmpT, FtsH, or combinations thereof. The engineered bacterium may further comprise deficient Lon and deficient OmpT.

The gene encoding the protease may be knocked out or knocked down in the engineered bacterium. The gene encoding the protease may be mutated or deleted in the engineered bacterium.

The protease may be deleted by replacing the protease gene with a selection marker, such as an antibiotic resistance gene. For example, the antibiotic may be kanamycin, chloramphenicol, tetracyclin, ampicillin, vancomycin or erythromycin. In one embodiment, the antibiotic is kanamycin.

The bacterium may belong to the *Escherichia, Methylomonas, Methylobacter, Methylococcus, Methylosinus, Salmonella, Erwina, Haematococcus, Rhodobacter, Myxococcus, Corynebacteria, Pseudomonas* or *Bacillus* genus. In one embodiment, the bacterium is *Escherichia coli*. For example, the *Escherichia coli* strain may be *E. coli* BL21 (DE3) or *E. coli* BL21.

The engineered bacterium may further comprise a nucleic acid sequence encoding a polypeptide for overexpression. The polypeptide may be heterologous or homologous to the bacterium.

The polypeptide may be an enzyme, a growth factor, a blood clotting factor, a hormone, or a transcription factor.

DETAILED DESCRIPTION OF THE INVENTION

The present disclosure provides host cells for reliable, high yield recombinant protein production, including unstable proteins. The present bacterial cells are able to produce (e.g., overexpress) higher levels of proteins (or polypeptides), compared to commonly used strains, such as *E. coli* BL21 (DE3). The proteins (or polypeptides) may be heterologous or homologous to the host cells. The present host cell (e.g., a bacterial cell) is deficient in at least one protease (or a subunit of a protease) such as Clp or ClpP. The host cell may also contain an expression vector that encodes a protein or polypeptide for production (e.g., overexpression).

The present host cells may be deficient in one or more of the following proteases (or subunits of protease): Clp, ClpP, ClpQ (HslV), ClpAP, ClpXP, ClpAXP, ClpYQ, ClpA, ClpX, ClpY (HslU), and combinations thereof.

The ClpP protease may be disrupted (mutated or deleted) in the host cell. In addition to ClpP, other protease(s) may also be disrupted. In one embodiment, the host cell (e.g., a bacterium) has at least ClpP and the Lon protease disrupted. In another embodiment, the host cell (e.g., a bacterium) has at least ClpP and the OmpT protease disrupted. In a third embodiment, the host cell (e.g., a bacterium) has at least ClpP, Lon and OmpT disrupted.

The expression level of a target protein in the present engineered host cell (with a disrupted protease or a subunit of a protease, e.g., ClpP or others as described herein) may be greater than about 1.1 fold, greater than about 1.2 fold, greater than about 1.3 fold, greater than about 1.4 fold, greater than about 1.5 fold, greater than about 1.6 fold, greater than about 1.7 fold, greater than about 1.8 fold, greater than about 1.9 fold, greater than about 2 fold, greater than about 3 fold, greater than about 4 fold, greater than about 5 fold, greater than about 6 fold, greater than about 8 fold, greater than about 10 fold, greater than about 12 fold, greater than about 14 fold, greater than about 15 fold, greater than about 16 fold, greater than about 18 fold, greater than about 19 fold, greater than about 20 fold, greater than about 25 fold, or greater than about 30 fold, of the expression level of the target protein in an unmodified host cell (with intact protease or a subunit of a protease) or a host cell not engineered with the deficient protease (or a subunit of a protease).

The present disclosure provides a method of producing a desired polypeptide in host cells deficient in at least one protease (or a subunit of a protease). The method may contain the following steps: (a) culturing the host cells in a culture medium to allow expression of the desired polypeptide in the host cells; and (b) isolating the desired polypeptide from the host cells.

In some embodiments, the present method comprises introducing an expression vector encoding a polypeptide (protein) into a host cell (e.g., a bacterial cell), thereby expressing the polypeptide.

Also encompassed by the present disclosure is a method for expressing (or overexpressing) a polypeptide (protein) in host cells. The method may contain the following steps: (a) transforming the engineered host cell (e.g., a bacterial cell) with a nucleic acid sequence encoding a polypeptide (protein), where the engineered host cell has at least one deficient protease (or a subunit of a protease); (b) culturing the host cell to produce the polypeptide (protein); and (c) isolating the polypeptide (protein).

The present disclosure provides a method of expressing a polypeptide (protein) in a host cell (e.g., a bacterial cell). The method may contain the following steps: (a) engineering a host cell to decrease level and/or activity of a protease (or a subunit of a protease); (b) transforming the engineered host cell with a nucleic acid sequence encoding a polypeptide (protein); (c) culturing the bacterium to produce the polypeptide (protein); and (d) isolating the polypeptide (protein). the context clearly dictates otherwise. Thus, for example, references to "a nucleic acid" includes one or more nucleic acids, and/or compositions of the type described herein which will become apparent to those persons skilled in the art upon reading this disclosure and so forth.

Proteases

In the present host cell, a protease (or a subunit of a protease) may be deficient or disrupted (mutated or deleted). The level and/or activity of the protease (or a subunit of a protease) in the present host cell is decreased compared to the cell which has the wild-type protease or the wild-type protease subunit. For example, an ATPase submit of a protease may be deficient. The protease or a subunit of a protease that may be deficient in the present host cells include, but are not limited to, a Clp protease, ClpP, ClpQ (HslV), ClpAP, ClpXP, ClpAXP, ClpYQ (HslUV), Lon, OmpT, FtsH (HflB), ClpA, ClpX, ClpY (HslU), or combinations thereof.

The present host cell may also be deficient in an ortholog or a homolog of the protease or (a subunit of a protease) as described herein.

One or more than one protease (or a subunit of a protease) may be disrupted in the present host cell, including 1, 2, 3, 4, 5, 6, 7, 8, 9, 10 or more proteases (or subunits of protease).

In addition to ClpP, other protease(s) may also be disrupted. In one embodiment, the bacteria have at least ClpP and the Lon protease disrupted. In another embodiment, the bacteria have at least ClpP and the OmpT protease disrupted. In a third embodiment, the bacteria have at least ClpP, Lon and OmpT disrupted.

The protease may be an ATP-dependent protease. The protease may be a serine protease.

The term "disruption" or "attenuation" means reducing or suppressing the activity or level of the protease (or a subunit of a protease) in the host cell.

The protease (or a subunit of a protease) may be deleted (partially or in its entirety), partially truncated, or mutated. The gene encoding the protease (or a subunit of a protease) may be deleted (partially or in its entirety), partially truncated, or mutated. The mutation in the protease may be a mutation of any type. For instance, the mutation may constitute a point mutation, a frame-shift mutation, an insertion, a deletion of part or all of the protease (or a subunit of a protease). In one embodiment, a portion of the bacterial genome encoding the protease (or a subunit of a protease) has been replaced with a polynucleotide (e.g., a heterologous polynucleotide). In another embodiment, the promoter of the gene encoding a protease or a subunit of a protease may contain one or more mutations. Examples of mutations include any mutation that introduces one or more stop codons within the coding region of a gene encoding the protease (or a subunit of a protease), any mutation that modifies the structure of the protease (or a subunit of a protease). The protease (or a subunit of a protease) may be disrupted, for example, by using a weak promoter for a gene encoding the protease (or a subunit of a protease), and/or using an allele which encodes a corresponding protease (or a subunit of a protease) which has a low activity or inactivates the corresponding protease (or a subunit of a protease).

The gene encoding the protease (or a subunit of a protease) may be knocked out or knocked down.

The term "knock out" means deleting or inactivating one or more genes in a genetically engineered cell.

The term "knock down" means reducing or attenuating the expression of one or more genes in a genetically engineered cell.

The protease (or a subunit of a protease) in the present host cells may be engineered to have attenuated, diminished or abrogated level and/or activity.

When a protease (or a subunit of a protease) is disrupted, the activity or level of the corresponding protease (or a subunit of a protease) may be reduced to, e.g., 0 to 75%, 0 to 50%, 0 to 25%, 0 to 10%, or 0 to 5% of the activity or level of the wild-type protease (or a subunit of a protease), or of the activity or level of the protease (or a subunit of a protease) in the starting cells before the protease or a subunit of a protease is attenuated.

The present host cell may also be deficient in another protein or DNA which results in a deficiency in a protease (or a subunit of a protease). For example, the present host cell may contain any mutation in a protein and/or DNA that decreases the transcription or translation of a protease (or a subunit of a protease). The present host cell may contain any mutation that directly or indirectly modifies post-transcription or post-translation process of a protease (or a subunit of a protease) so that modifies its expression or activity.

In one embodiment, the present host cell contains a compound or entity, e.g., antisense RNA that decreases the transcription and/or translation of a protease (or a subunit of a protease), or decreases the activity or function of a protease (or a subunit of a protease). In certain embodiments, altered gene expression and/or protease activity may be accomplished using, e.g., antisense RNA, siRNA, miRNA, ribozymes, triple stranded DNA, nucleic acids, small molecules, protease inhibitors, a transposon, and other manipulations for altered gene expression and/or activity.

When disrupting a protease (or a subunit of a protease), the disruption (e.g., mutation, deletion, or inactivation) may be detected by a selection marker so that the modified host cells can be identified and isolated. The protease (or a subunit of a protease) may be deleted by replacing the protease gene with a selection marker.

The selection marker may be any suitable marker gene such as an antibiotic resistance gene or an auxotrophic marker. The antibiotics that can be used to select the host cells having the antibiotic resistance genes include, but are not limited to, kanamycin, chloramphenicol, tetracyclin, ampicillin, vancomycin and erythromycin or any other representatives of the beta-lecterns, the aminoglycosides, the glycopeptides or the macrolide antibiotics.

In one embodiment, the present bacteria are constructed by P1 transduction of a clpP::kan from the KEIO collection into BL21(DE3). This results in the genotype of the bacteria being BL21(DE3) plus a clpP::kan mutation (a kan insert in the clpP gene derived from the KEIO collection). The $E.\ coli$ B strains obtained may be $E.\ coli$ B BL21(DE3) clpP::kan or $E.\ coli$ B BL21(DE3) AclpP. In one embodiment, the bacteria may be F-ompT hsd$S_B$ ($r_B$-$m_B$-) gal dcm (DE3) clpP::kan.

Host Cells Including Bacteria

The host cell producing the protein(s) or polynucleotide(s) of interest can be any host cell. The present host cells may be prokaryotic or eukaryotic. In some embodiments, the host cell is a bacterial cell. In some embodiments, the host cell is a yeast cell. In some embodiments, the cells are mammalian cells. In some embodiments, the cells are antigen-presenting cells, such as dendritic cells. In some embodiments, the host cells are isolated.

The present bacteria can be from any species or strain.

Prokaryotes to use in the present systems and methods include eubacteria, such as Gram-negative or Gram-positive organisms, for example, Enterobacteriaceae such as *Escherichia* (e.g., *E. coli*), *Enterobacter, Erwinia, Klebsiella, Proteus, Salmonella*, e.g., *S. typhimurium, Serratia*, e.g., *S. marcescans*, and *Shigella*, as well as Bacilli, *Pseudomonas* such as *P. aeruginosa*, and *P. fluorescens, Ralstonia*, e.g., *R. eutropha, Staphylococcus*, e.g. *S. carnosus*, and *Streptomyces*.

The bacterium may be in the Enterobacteriaceae family which includes, but are not limited to, bacteria belonging to the genera *Escherichia, Enterobacter, Erwinia, Klebsiella, Pantoea, Photorhabdus, Providencia, Salmonella, Serratia, Shigella, Geobacillus, Morganella Yersinia*, etc. Specifically, those classified into the Enterobacteriaceae according to the taxonomy used in the NCBI (National Center for Biotechnology Information) database can be used.

In some embodiments, the present bacterium belongs to the genus *Escherichia, Bacillusm*, or *Pantoea*.

Non-limiting examples of bacteria belonging to the genus *Escherichia* include bacteria described by Neidhardt et al. (*Escherichia coli* and *Salmonella typhimurium*, American Society for Microbiology, Washington D.C., 1208, Table 1).

In one embodiment, the present bacterium may be *Escherichia coli* (*E. coli*). They include, but are not limited to, *E. coli* B strains, K-12 strains, C strains, and W strains. The bacterial strains include, but are not limited to, BL21, BL21(DE3), BL21(DE3)pLysS, BL21(DE3)pLysE, and BL21(AI). The *E. coli* strain B BL21 (DE3) is described in Studier et al., J. Mol. Biol. (1986) 189:113-130 and Studier et al. Methods in Enzymology (1990) 185:60-89. The *E. coli* strain B BL21 (DE3) is commercially available (e.g., New England BioLabs, Stratagene and Novagen). Non-limiting examples of the *E. coli* K-12 strains include AD494, Origami™ (Novagen), and HMS 174. Derman et al., (1993) Mutations that allow disulfide bond formation in the cytoplasm of *Escherichia coli*. Science 262 1744-1747. Campbell et al., (1978) Genetic recombination and complementation between bacteriophage T7 and cloned fragments of T7 DNA. Proc. Natl. Acad. Sci. U.S.A. 75 2276-2280. Non-limiting examples of the strains of *E. coli* also include, *E. coli* 294 (ATCC 31,446), *E. coli* B, *E. coli* X1776 (ATCC 31,537), *E. coli* W31 10 (ATCC 27,325), and CY15070 (Paluh et al., Nucl. Acids Res. 24; 14(20): 7851-60 (1986); (ATCC #47022)). U.S. Pat. No. 8,535,909.

Non-limiting examples of bacteria belonging to the genus *Pantoea* include *Pantoea agglomerans, Pantoea ananatis, Pantoea stewartii* and the like.

Non-limiting examples of bacteria belonging to the genus *Bacillus* include *B. subtilis, B. megaterium, B. amyloliquefaceins, B. thuringiensis, B. licheniformis, B. sphericus, B. anthracis, B. cereus, B. lentus, B. brevis, B. stearothermophilus, B. alkalophilus, B. amyloliquefaciens, B. clausii, B. halodurans, B. megaterium, B. coagulans, B. circulans, B. lautus, B. pumilus, B. thuringiensis* etc. As used herein, "*Bacillus* sp." includes all species within the genus *Bacillus*. In some embodiments, the *Bacillus* strain of interest is an alkalophilic *Bacillus*. Numerous alkalophilic *Bacillus* strains are known (See e.g., Aunstrup et al., Proc IV IFS: Ferment. Tech. Today, 299-305 [1972]). Numerous *B. subtilis* strains are known (See e.g., 1A6 (ATCC 39085), 168 (1A01), SBI9, W23, Ts85, B637, PB1753 through PB1758, PB3360, JH642, 1A243 (ATCC 39,087), ATCC 21332, ATCC 6051, M1113, DE100 (ATCC 39,094), GX4931, PBT 110, and PEP 211 strain; Hoch et al., Genetics, 73:215-228 [1973]). Palva et al., Gene, 19:81-87 [1982]; Fahnestock and Fischer, J. Bacteriol., 165:796-804 [1986]; and Wang et al, Gene 69:39-47 [1988].

In some embodiments, the bacteria are members of the genus *Bacillus*. In another embodiment, the bacteria are *Bacillus anthracis*. In still another embodiment, the bacteria are *Yersinia pestis*. In other embodiments of the invention, the bacteria are from the genus *Salmonella*. In some embodiments, the bacteria are *Salmonella typhimurium*. In some embodiments, the bacteria belong to the genus *Shigella*. For instance, in some embodiments, the bacteria are *Shigella flexneri*. In some embodiments, the bacteria are members of the genus *Brucella*. In an alternative embodiment, the bacteria are mycobacteria. The mycobacteria are optionally a member of the species *Mycobacterium tuberculosis*. In some embodiments, the bacteria are *Bacillus* Calmette-Guerin (BCG). In some embodiments, the bacteria are *E. coli*. In some embodiments, the bacteria may be *Listeria, Bacillus anthracis, Yersinia pestis, Salmonella*, and mycobacteria.

Examples of prokaryotic host cells also include, but are not limited to, *Salmonella typhimurium, Bacillus subtilis, Bacillus licheniformis, Bacillus megaterium, Bacillus brevi, Pseudomonas aeruginosa, Pseudomonas fluorescens, Ralstonia eutropha, Staphylococcus carnosus* and *Serratia marcescans*.

Examples of host cells also include, but are not limited to, *Acinetobacter, Agrobacterium tumefaciens, Azoarcus, Bacillus anthracis, Bacillus clausii, Bacillus licheniformis, Bacillus amyloliquefaciens, Bacillus subtilis, Bacillus lentus, Bacillus halodurans, Bifidobacterium longum, Buchnera aphidicola, Campestris, Campylobacter jejuni, Clostridium perfringens, Escherichia coli, Erwinia carotovora, Francisella tularensis, Haemophilus influenzae, Helicobacter pylori, Mycobacterium tuberculosis, Neisseria meningitides, Pseudomonas aeruginosa, Prochlorococcus marinus, Streptococcus pneumoniae, Salmonella enterica, Shewanella oneidensis, Salmonella enterica, Salmonella typhimurium, Staphylococcus epidermidis, Staphylococcus aureus, Shigella flexneri, Streptomyces coelicolor, Streptomyces lividans, Tropheryma whipplei, Tularensis, Temecula, Thermosynechococcus elongates, Thermococcus kodakarensis, Xanthomonas axonopodis, Xanthomonas campestris; Xylella fastidiosa* and *Yersinia pestis* host cells.

The starting host cell in which a protease (or a subunit of a protease) is then disrupted may be from a non-recombinant strain, mutants of a naturally-occurring strain, or a recombinant strain that is modified to be deficient in a protease.

In some embodiments, the bacteria are attenuated. In some embodiments, the bacteria are attenuated for cell-to-cell spread, entry into non-phagocytic cells, and/or proliferation (relative to a bacterium without the attenuating mutation). The bacteria may be attenuated by mutation or by other modifications.

The microorganisms prepared according to the invention can be cultured continuously or discontinuously in the batch process (batch culture), or in the fed batch (feed process), or repeated fed batch process (repetitive feed process) for the purpose of production of the protein or polypeptide of interest.

The culture of the recombinant microorganisms according to the present invention may be carried out according to a method well known in the art. Culture conditions, including culture temperature, time and the pH of medium can be suitably controlled. The collection of recombinant microbial cells from the culture broth can be carried out using conventional isolation techniques, for example, centrifugation or filtration.

The medium used for culturing the present host cells may be either a synthetic medium or a natural medium. In one embodiment, the medium includes a carbon source and a nitrogen source and minerals and, if necessary, appropriate amounts of nutrients which the host cells require for growth. The culture medium to be used must meet the requirements of the particular strains in a suitable manner. Descriptions of culture media for various microorganisms are contained in Manual of Methods for General Bacteriology of the American Society for Bacteriology (Washington D.C., USA, 1981). Sugars and carbohydrates, such as e.g. glucose, sucrose, lactose, fructose, maltose, molasses, starch and cellulose, oils and fats, such as e.g. soya oil, sunflower oil, groundnut oil and coconut fat, fatty acids, such as e.g. palmitic acid, stearic acid and linoleic acid, alcohols, such as e.g. glycerol and ethanol, and organic acids, such as e.g. acetic acid, can be used as the source of carbon. These substances can be used individually or as a mixture. Organic nitrogen-containing compounds, such as peptones, yeast extract, meat extract, malt extract, corn steep liquor, soya bean flour and urea, or inorganic compounds, such as ammonium sulfate, ammonium chloride, ammonium phosphate, ammonium carbonate and ammonium nitrate, can be used as the source of nitrogen. The sources of nitrogen can be used individually or as a mixture. Phosphoric acid, potassium dihydrogen phosphate or dipotassium hydrogen phosphate or the corresponding sodium-containing salts can be used as the source of phosphorus. The culture medium may comprise salts of metals, such as e.g. magnesium sulfate or iron sulfate. Growth substances, such as amino acids and vitamins, may be employed. Suitable precursors can moreover be added to the culture medium. The starting substances mentioned can be added to the culture in the form of a single batch, or can be fed in during the culture in a suitable manner.

The proteins or polypeptides to be produced in the host cells can be synthesized as fusion peptides, secreted into the media or into the periplasmic space, produced in free form in the cytoplasm, or accumulated in intracellular bodies such as in inclusion bodies. The host cell may or may not secrete the polypeptides of interest.

Purification of the proteins or polypeptides involves the use of conventional methodologies which may be adapted by conventional techniques to the protein (or polypeptide) of interest.

Polypeptides/Proteins to be Expressed or Overexpressed

A "desired polypeptide (protein)", "polypeptide (protein) of interest," or "target polypeptide (protein)" refers to the protein/polypeptide to be expressed (e.g., overexpressed) by the host cell.

The engineered (recombinant) bacteria may constitutively or inducibly express one or more of proteins/polypeptides. The gene of the protein/polypeptides may be under the control of a constitutive or inducible promoter.

The desired polypeptide (or polypeptide of interest) may be either homologous or heterologous to the host. As used herein, the term "heterologous protein" refers to a protein or polypeptide that does not naturally occur in the host cell. Similarly, a "heterologous polynucleotide" refers to a polynucleotide that does not naturally occur in the host cell. The target polypeptide (protein) may be a heterologous polypeptide (protein) which cannot be normally found in transformed host cells expressing the protein.

The desired polypeptide may be an enzyme, a transcription factor, a hormone, a growth factor, a receptor, vaccine, an antibody or its fragment, or the like.

The desired polypeptide/protein may be an enzyme, including, but not limited to, amylolytic enzymes, proteolytic enzymes, cellulytic enzymes, oxidoreductase enzymes, cellulose, plant wall degrading enzymes, amylases, proteases, xylanases, lipases, laccases, phenol oxidases, oxidases, cutinases, cellulases, hemicellulases, esterases, perioxidases, catalases, glucose oxidases, phytases, pectinases, glucosidases, isomerases, transferases, galactosidases and chitinases.

Proteins (or polypeptides) that may be produced (e.g., overexpressed) by the present host cells and methods include, but are not limited to, growth factors (e.g. epidermal growth factor, insulin-like growth factor-1); blood clotting factors (e.g. anti-hemophilic factor); hormones (e.g., insulin, glucagon, growth hormone, somatotropin, erythropoietin); cytokines (e.g., interferons, interleukins; granuloctye colony-stimulating factor, granulocyte-macrophage colony-stimulating factor, CD86); chemokines (e.g., CCL3); receptors (e.g., chemokine receptors, tyrosine kinase receptors); enzymes (e.g., proteases, lipases, carbohydrases, chymosin, DNAase, prourokinase, arginine deaminase, cytosine deaminase, L-asparaginase); enzyme activators (e.g., tissue-type plasminogen activator); enzyme inhibitors (e.g, tissue inhibitors of metalloproteases); peptides (e.g., hirudin, neuregulin-1 fragments); antibody fragments (e.g., Fab fragments); protein scaffolds (e.g. Adnectins, Affibodies, Anticalins, DARPins, engineered Kunitz-type inhibitors, tetranectins, A-domain proteins, lipocalins, repeat proteins such as ankyrin repeat proteins, immunity proteins. $\alpha 2p8$ peptide, insect defensin A, PDZ domains, charybdotoxins, PHD fingers, TEM-1$\beta$-lactamase, fibronectin type III domains, CTLA-4, T-cell resptors, knottins, neocarzinostatin, carbohydrate binding module 4-2, green fluorescent protein, thioredoxin); vaccines (e.g. influenza vaccines, anthrax vaccines such as rPA vaccines, hepatitis E virus vaccines such as ORF2 vaccines, human papilloma virus vaccines); toxins; and immunotoxins (Misawa and Kumagai, Biopolymers 51: 297-307 (1999); Zhang et al, Protein Expr. Purif. 25(1): 105-13 (2002); Demain, Trends in Biotech. 18(1): 26-31 (2000); Gebauer & Skerra, Curr. Opin. Chem. Biol. 13:245-55 (2009); Gill & Damle, Curr. Opin. Biotech 17: 653-58 (2006); Hosse et al, Protein Sci. 15:14-27 (2006); Skerra, Curr. Opin. Biotech 18: 295-3-4 (2007); Song et al, PLoS ONE 3(5): e2257 (2008); Vahedi et al, Applied Biochem. and Biotech. 157(3): 554-61 (2009); Hakim and Benhar, MAbs. 1(3): 281-87 (2009)).

Proteins (or polypeptides) that may be produced by the present host cells and methods include, but are not limited to, hGH, glucagon-like peptides, interleukins, insulin analogs, adiponectin, FGF-21, trypsin, aprotinin, amylin, leptin and analogs thereof, enzymes such as sialidase, transglutaminase (tGase), HRV (Human Rhino Virus) 3C protease, Tobacco Etch Virus (TEV) protease and variants thereof.

In some embodiments, the protein/polypeptide expressed by the present host cells is an antibody or an antibody fragment, such as an Fv, a disulfide-linked Fv, an scFv, a kappa light chain fragment, a lambda light chain fragment, and a Fab fragment.

One or more polypeptides and/or proteins may be produced. The polynucleotides encoding the polypeptides/proteins may be on different expression vectors or may be on the same expression vector.

The polynucleotide encoding the polypeptide/protein of interest may be operably linked to regulatory sequences, such as promoters, enhancers or one or more other transcriptional regulatory sequences, optionally as part of a vector comprising these sequences.

Vectors

The present host cell may comprise at least one vector (e.g., a plasmid) comprising at least one nucleotide sequence encoding a (heterologous or homologous) protein (or polypeptide). The invention also provides a method of expression, wherein a (heterologous or homologous) protein can be expressed in the host cells.

The vectors may contain regulatory sequences, e.g., transcriptional or translational control sequences required for expressing the exogenous polypeptide. Suitable regulatory sequences include but are not limited to replication origin, promoter, enhancer, repressor binding regions, transcription initiation sites, ribosome binding sites, translation initiation sites, and termination sites for transcription and translation. One or more regulatory sequences may be operably linked to the gene encoding the protein (or polypeptide) to be expressed in the host cells.

The term "recombinant" when used in reference to a cell, nucleic acid, protein or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express nucleic acids or polypeptides that are not found within the native (non-recombinant) form of the cell or express native genes that are otherwise abnormally expressed, under-expressed, overexpressed or not expressed at all. A "recombinant protein" is a protein made using recombinant techniques, i.e., through the expression of a recombinant nucleic acid as depicted above. As used herein, "recombinant host cells" and "engineered host cells" are used interchangeably; "recombinant bacterium" and "engineered bacterium" are used interchangeably.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. A number of bacterial expression vectors are available commercially and through the American Type Culture Collection (ATCC), Rockville, Md.

Tags can also be added to recombinant proteins to increase protein stability and/or provide convenient methods of isolation, e.g., SUMO, c-myc, biotin, poly-Histidine (His), etc.

A nucleic acid sequence may be introduced into a cell by transformation, transfection, transduction, or other suitable techniques. Transformation of a bacterium with a DNA coding for a target protein means introduction of the DNA into a bacterium cell to increase expression of the gene coding for the target protein.

Bacterial transformation may be referred to as genetic alteration of a bacterial cell resulting from the uptake of exogenous genetic material (exogenous DNA) from its surroundings through the cell membrane. For transformation to occur, bacteria should be in a state of competence. Some bacteria are naturally capable of taking up DNA under laboratory conditions. For other bacteria, Artificial competence can be induced in laboratory procedures that involve making the cell passively permeable to DNA by exposing it to conditions that do not normally occur in nature. In one embodiment, chilling cells in the presence of divalent cations (such as $Ca^{2+}$, $Mg^{2+}$) prepares the cell walls to become permeable to plasmid DNA. Cells are incubated on ice with the DNA and then briefly heat shocked. Electroporation is another approach to promote competence of the bacterial cells, where the cells are briefly shocked with an electric field. Green & Sambrook, Molecular Cloning, A Laboratory Manual (4th edition, 2012); Kriegler, Gene Transfer and Expression: A Laboratory Manual (1990); and Current Protocols in Molecular Biology (Ausubel et al., eds., 1994).

Increased Protein/Polypeptide Production

The present host cell, with disrupted protease (or a subunit of a protease), produces a target protein in an amount that is greater compared to a cell in which the protease (or a subunit of a protease) has not been disrupted.

The expression level of the target protein in the present host cell (with disrupted protease or a subunit of a protease, e.g., ClpP or others as described herein) may be greater than about 1.1 fold, greater than about 1.2 fold, greater than about 1.3 fold, greater than about 1.4 fold, greater than about 1.5 fold, greater than about 1.6 fold, greater than about 1.7 fold, greater than about 1.8 fold, greater than about 1.9 fold, greater than about 2 fold, greater than about 3 fold, greater than about 4 fold, greater than about 5 fold, greater than about 6 fold, greater than about 8 fold, greater than about 10 fold, greater than about 12 fold, greater than about 14 fold, greater than about 15 fold, greater than about 16 fold, greater than about 18 fold, greater than about 19 fold, greater than about 20 fold, greater than about 25 fold, greater than about 30 fold, about 2 fold-10 fold, about 2 fold-5 fold, about 1.5 fold-8 fold, about 2 fold-8 fold, about 5 fold-15 fold, about 5 fold-20 fold, about 2 fold-30 fold, about 2 fold-20 fold, about 5 fold-20 fold, or about 5 fold-10 fold, of the expression level of the target protein in an unmodified host cells (with intact or undisrupted protease or a subunit of a protease) or a host cell not engineered with the deficient protease (or a subunit of a protease).

The expression level of the target protein in the present bacteria (with disrupted protease or a subunit of a protease, e.g., ClpP or others as described herein) may be increased by at least 20%, about 30%, about 40%, about 50%, about 60%, about 70%, about 75% about 80%, about 85%, about 90%, about 95%, about 100%, about 125%, about 150%, about 175%, about 200% or about 250% as compared to the expression level of the target protein in the unmodified host bacteria (with intact protease or a subunit of a protease) or a host cell not engineered with the deficient protease (or a subunit of a protease).

To quantitate the yield or amount of a protein (or polypeptide) produced by host cells, conventional methods such as immunoassay, high performance liquid chromatography (HPLC), enzymatic activity, spectrophotometric techniques, SDS-PAGE and the like can be employed.

Pharmaceutical Compositions

A variety of different compositions such as pharmaceutical compositions, probiotic compositions, immunogenic compositions, and vaccines are also provided by the present disclosure. These compositions may comprise proteins (or polypeptides) produced by the present host cells. These compositions may comprise the present host cells (e.g., engineered bacteria described herein).

In one embodiment, the present disclosure provides a pharmaceutical composition comprising the following: (i) proteins (or polypeptides) produced by the present host cells; and (ii) a pharmaceutically acceptable carrier.

In another embodiment, the present disclosure provides a pharmaceutical composition comprising the following: (i) the present host cells (e.g., engineered bacteria described herein); and (ii) a pharmaceutically acceptable carrier.

Pharmaceutically acceptable carriers include any and all solvents, dispersion media, vehicles, coatings, diluents, antifungal agents, isotonic and absorption delaying agents, buffers, carrier solutions, suspensions, colloids, and the like. Pharmaceutically acceptable carriers are well known to those of ordinary skill in the art, and include any material which, when combined with an active ingredient, allows the ingredient to retain biological activity. For instance, pharmaceutically acceptable carriers include, but are not limited to, water, buffered saline solutions (e.g., 0.9% saline), emulsions such as oil/water emulsions, and various types of wetting agents. Possible carriers also include, but are not limited to, oils (e.g., mineral oil), dextrose solutions, glycerol solutions, chalk, starch, salts, glycerol, and gelatin.

While any suitable carrier known to those of ordinary skill in the art may be employed in the pharmaceutical compositions, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. In some embodiments, for parenteral administration, such as subcutaneous injection, the carrier comprises water, saline, alcohol, a fat, a wax or a buffer. In some embodiments, any of the above carriers or a solid carrier, such as mannitol, lactose, starch, magnesium stearate, sodium saccharine, talcum, cellulose, glucose, sucrose, and magnesium carbonate, are employed for oral administration.

Compositions comprising such carriers may be formulated by conventional methods (see, for example, Remington's Pharmaceutical Sciences, 18th edition, A. Gennaro, ed., Mack Publishing Co., Easton, Pa., 1990; and Remington, The Science and Practice of Pharmacy 20th Ed. Mack Publishing, 2000).

The present invention also provides for a probiotic composition comprising the present engineered (recombinant) bacteria and/or proteins (or polypeptides) produced by the present host cells. The engineered (recombinant) bacteria may constitutively or inducibly express one or more of proteins/polypeptides. In one embodiment, the proteins/polypeptides expressed are involved in carbohydrate metabolism and/or transport. In certain embodiments, the proteins can include a glycoside hydrolase, a galactokinase and a glucose/galactose transporter. The gene of the protein/polypeptides may be under the control of a constitutive or inducible promoter.

The probiotic composition may be administered enterally, such as oral, sublingual and rectal administrations.

The probiotic composition can be a food composition, a beverage composition, a pharmaceutical composition, or a feedstuff composition.

The probiotic composition may comprise a liquid culture. The probiotic composition may be lyophilized, pulverized and powdered. As a powder it can be provided in a palatable form for reconstitution for drinking or for reconstitution as a food additive. The composition can be provided as a powder for sale in combination with a food or drink. The food or drink may be a dairy-based product or a soy-based product. Typical food products that may be prepared in the present disclosure may be milk-powder based products; instant drinks; ready-to-drink formulations; nutritional powders; milk-based products, such as yogurt or ice cream; cereal products; beverages such as water, coffee, malt drinks; culinary products and soups.

The composition may further contain at least one prebiotic. "Prebiotic" means food substances intended to promote the growth of probiotic bacteria in the intestines.

The compositions can be, e.g., in a solid, semi-solid, or liquid formulation. Compositions can also take the form of tablets, pills, capsules, semisolids, powders, sustained release formulations, emulsions, suspensions, or any other appropriate compositions.

The present composition may be in the form of: an enema composition which can be reconstituted with an appropriate diluent; enteric-coated capsules or microcapsules; powder for reconstitution with an appropriate diluent for naso-enteric infusion, naso-duodenal infusion or colonoscopic infusion; powder for reconstitution with appropriate diluent, flavoring and gastric acid suppression agent for oral ingestion; or powder for reconstitution with food or drink.

The composition may also contain conventional pharmaceutical additives and adjuvants, excipients and diluents, including, but not limited to, water, gelatine of any origin, vegetable gums. ligninsulfonate, talc, sugars, starch, gum arabic, vegetable oils, polyalkylene glycols, flavouring agents, preservatives, stabilizers, emulsifying agents, buffers, lubricants, colorants, wetting agents, fillers, and the like. In all cases, such further components will be selected having regard to their suitability for the intended recipient.

Immunogenic compositions are also provided by the present disclosure. For instance, the invention provides an immunogenic composition comprising a recombinant bacterium described herein and/or proteins (or polypeptides) produced by the present host cells. In some embodiments, the immunogenic composition comprises recombinant bacteria, wherein a polypeptide expressed by the recombinant bacteria is an antigen or comprises an antigen. In some embodiments, the recombinant bacterium in the immunogenic composition expresses the polypeptide comprising the antigen at a level sufficient to induce an immune response to the antigen upon administration of the composition to a host (e.g., a mammal such as a human).

An additional application of the present host cells and methods is creating synthetic organisms. Synthetic organisms can be used for a variety of purposes, including industrial enzyme production, biofuel and electrical energy production, vaccine development, and anticancer therapies.

The following are examples of the present disclosure and are not to be construed as limiting.

Example 1

To produce recombinant NunΔN, *E. coli* BL21(DE3) with a clpP::kan mutation was transformed with a construct encoding SUMO-NunΔN. After purification of SUMO-NunΔN, SUMO was cleaved using the SUMO protease Ulp-1.

The engineered bacteria were constructed by P1 transduction of a clpP::kan from the KEIO collection into BL21 (DE3). This resulted in the genotype of the bacteria being BL21(DE3) plus a clpP::kan mutation (a kan insert in the clpP gene derived from the KEIO collection). The *E. coli* B strains obtained may be *E. coli* B BL21(DE3) clpP::kan or *E. coli* B BL21(DE3) ΔclpP. In one embodiment, the bacteria may be F-ompT hsdS$_B$ (r$_B$-m$_B$-) gal dcm (DE3) clpP::kan.

The P1 transduction may be conducted according to any suitable protocol. Current Protocols in Molecular Biology, 2007, Unit 1.17 *E. coli* Genome Manipulation by P Transduction. In one embodiment, BL21 (DE3) cells are grown overnight in LB broth at 37° C. The cell pellet is harvested by centrifugation and re-suspended in 10 mM MgSO$_4$. The cells are then infected with the P1 bacteriophage grown on the KEIO strain (50 μl phage/100 μl cells). After 30 minutes at 37° C., 1 M sodium citrate is added and the mixture is plated on LB+kanamycin plates (50 ug/ml) at 37° C.

Although a very low level of SUMO-NunDN (SUMO-NunΔN) was produced in BL21 (DE3), SUMO-NunDN was produced at a much higher level in BL21(DE3) with a clpP::kan mutation. As the BL21 (DE3) strain is also deficient in Lon protease and OmpT protease, the BL21(DE3) with a clpP::kan mutation is deficient in Lon protease and OmpT protease, as well as ClpP protease.

Specifically, 12 liters frozen stock of the BL21(DE3) cells with a clpP::kan mutation that were transformed with plasmids encoding Sumo-NunΔN were thawed, and were induced with 0.5 mM IPTG when OD reached 0.8-1.0 (37° C.). The cells were then grown for about 4 additional hours at a lower temperature (e.g., 30° C.) with 180 rpm shaking.

Sumo-NunΔN has a molecular weight of approximately 24.5 kDa, and a pI of 6.49. After cleavage by the SUMO protease Ulp-1, the peptide NunΔN has a molecular weight of approximately 10.5 kDa, with a pI of 8.96.

In this experiment, Sumo-NunΔN is also polyhistidine tagged at the N-terminus. The sequence of polyhistidine-tagged Sumo-NunΔN is (SEQ ID NO:1):

MGHHHHHHHHHHSSGHIEGRHMASMSDSEVNQEAKPEVKPEVKPETHINL

KVSDGSSEIFFKIKKTTPLRRLMEAFAKRQGKEMDSLRFLYDGIRIQADQ

TPEDLDMEDNDIIEAHREQIGGSLESRDRRRIARWEKRIAYALKNGVTPG

FNAIDDGPEYKINEDPMDKVDKALATPFPRDVEKIEDEKYEDVMHRVVNH

AHQRNPNKKWS

Buffers

Lysis buffer: 50 mM Na-phosphate, pH7.9, 200 mM NaCl, 1 mM PMSF
Ni-A buffer: 50 mM Na-phosphate, pH7.9, 200 mM NaCl
Ni-B buffer: 50 mM Na-phosphate, pH7.9, 200 mM NaCl, 250 mM imidazole
MonoS-A buffer: 50 mM Na-phosphate, pH7.5, 1 mM DTT
MonoS-B buffer: 50 mM Na-phosphate, pH7.5, 1M NaCl, 1 mM DTT
GF buffer: 1×TGE, 0.2M NaCl, 5 mM DTT On day 1, cell pellet was resuspended in approximately 150 ml Lysis buffer. Cells were lysed using French Press. The cell debris was removed by centrifugation at 15,000 rpm for 25 min at 4'C. The centrifugation was repeated once, and the supernatant was used in the subsequent steps for protein purification.

Two of 5 ml HiTrap IMAC columns (GE Healthcare Life Sciences) were charged with and equilibrated with 3 column volumes (CV) of Ni-B and Ni-A buffer. The supernatant from the centrifugation was loaded onto the equilibrated column at a flow rate of 1 ml/min. The column was first washed with 4% Ni-B buffer (10 mM imidazole), 8% Ni-B buffer (20 mM imidazole), 16% Ni-B buffer (40 mM imidazole), and then eluted with gradient 20%-70%, and increased to 1000/a Ni-B buffer over 12 CV. 5-ml fractions were collected.

Figure 1A:
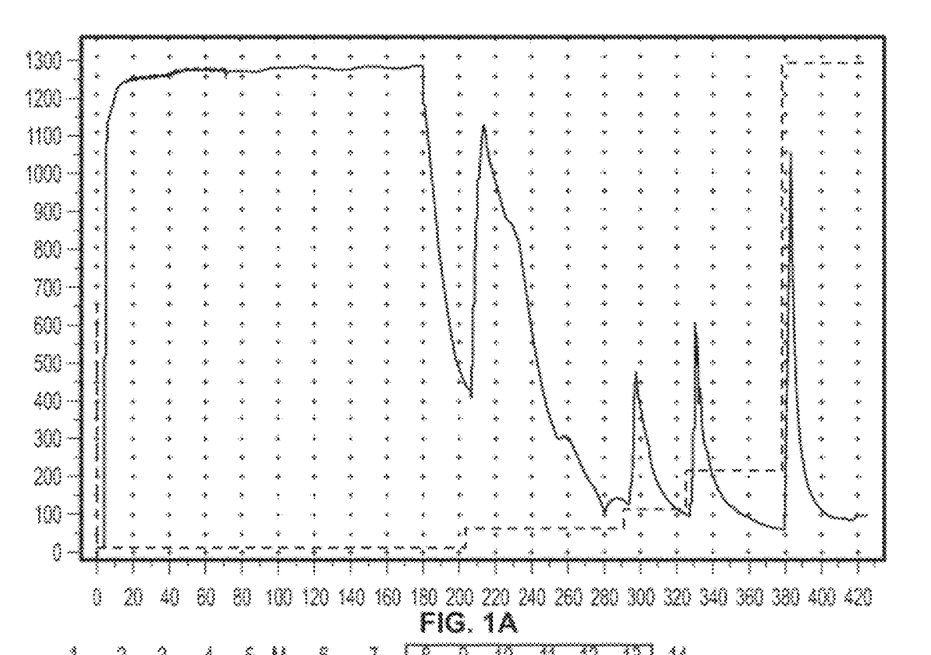
FIG. 1A shows a chromatogram of purification of SUMO-NunΔN (SUMO-NunDN) using the HiTrap IMAC column (GE Healthcare Life Sciences). The column was eluted with gradient 20%-100% Ni-B buffer over 12 CV (column volumes). 5-ml fractions were collected.
Figure 1B:
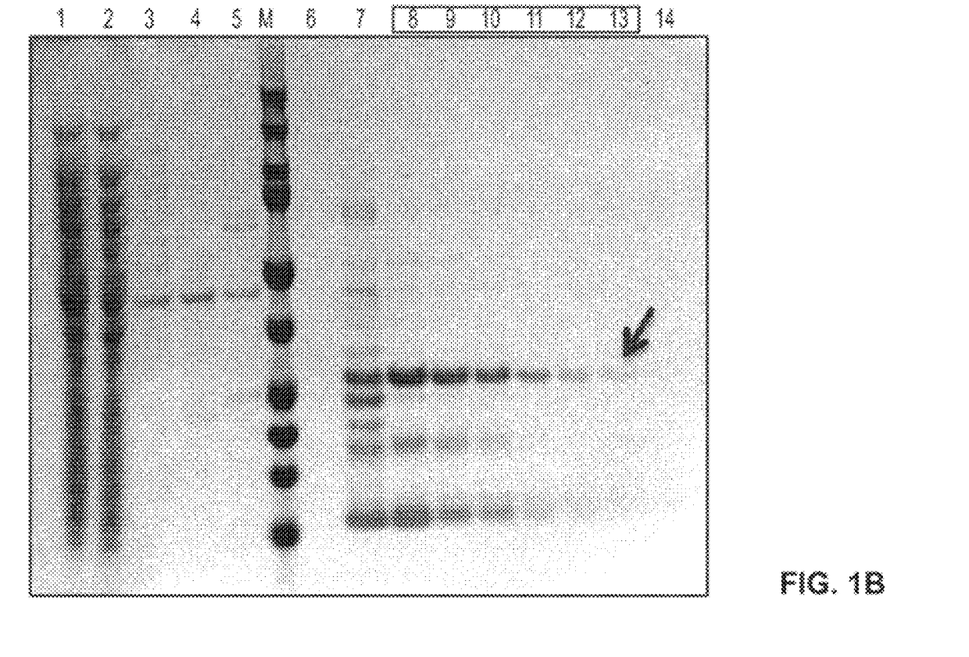
FIG. 1B shows SDS-PAGE analysis of samples of different fractions from the HiTrap IMAC column. Fractions 8-13 were collected for digestion by Ulp-1. Lane 1: Supernatant; Lane 2: Flow-through; Lane 3: 4% Ni-B wash; Lane 4: 8% Ni-B wash; Lane 5: 16% Ni-B wash; Lane 6: elution in a 10-ml fraction; Lanes. 7-14: 5-ml eluted fractions. The arrow points to the SUMO-NunDN band on the SDS-PAGE.

Samples of different fractions were run on SDS-PAGE (FIG. 1B). Based on the SDS-PAGE results, Fractions 8-13 were pooled for digestion by Ulp-1.

2 mM DTT and 0.9 mg Ulp-1 were added to 15 mg SUMO-NunΔN, and cleavage carried out. Alternatively, 1 mg Ulp-1 can be added to 25 mg SUMO-NunΔN.

The sample was added into a dialysis bag with a 3.5 kDa MWCO (molecular-weight cutoff) and was dialyzed against 1 L MonoS Buffer at 4° C. overnight.

An optional step after Ulp-1 cleavage is to centrifuge the sample for a short-period of time (e.g., 15,000 rpm for 10 min at 4° C.).

On day 2, SDS-PAGE was run to confirm completion of the cleavage. The sample was diluted 3-fold by the MonoS buffer, and loaded onto the equilibrated MonoS column (GE Healthcare Life Sciences). The MonoS column was washed with 10% MonoS-A buffer, and eluted with gradient 10-100%/MonoS-B buffer over 18 CV. 4-ml fractions were collected.

Figure 2A:
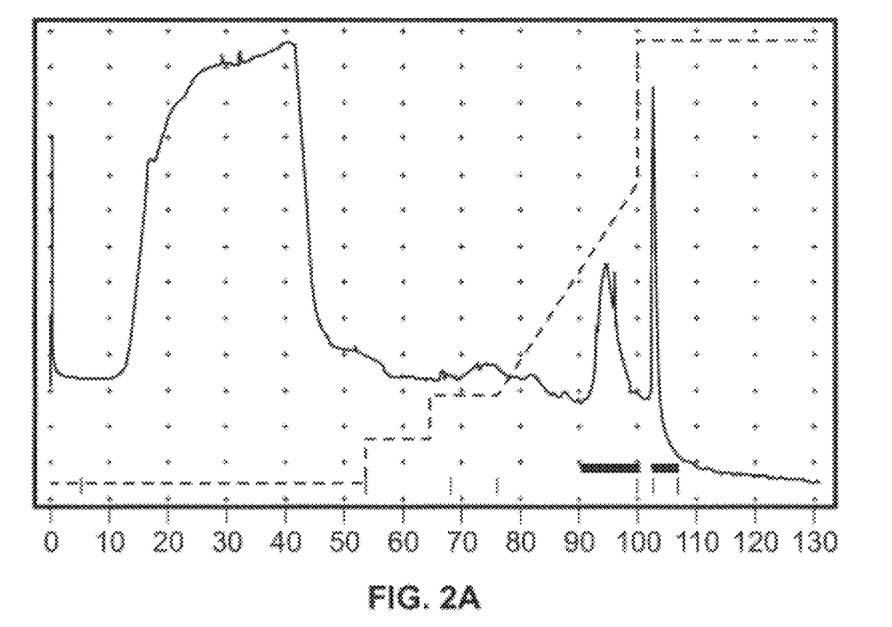
FIG. 2A shows a chromatogram of purification of NunΔN (NunDN) using the Mono S column (GE Healthcare Life Sciences) after SUMO is cleaved. The column was eluted with gradient 10-100% MonoS-B buffer over 18 CV.
Figure 2B:
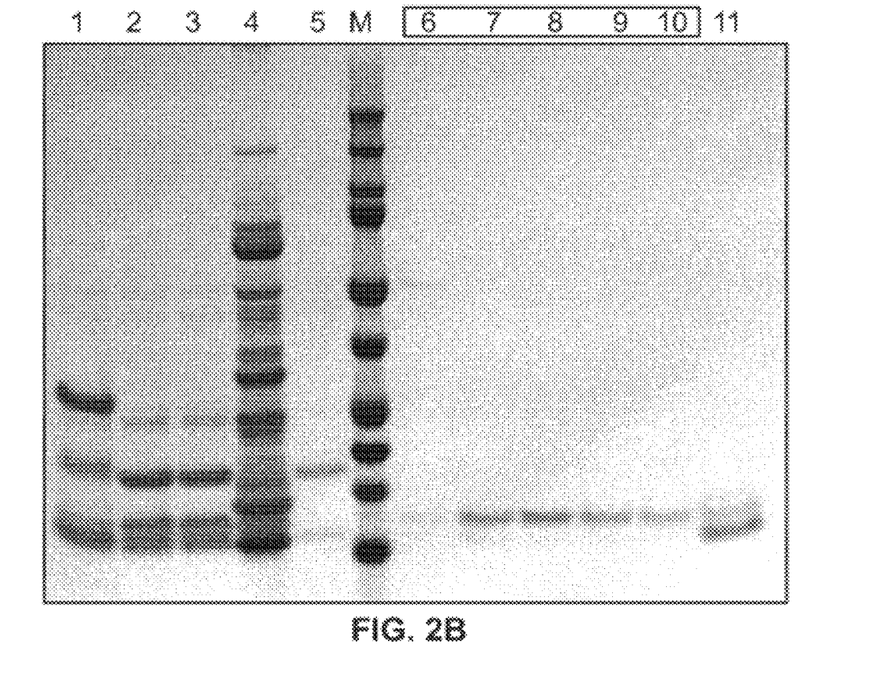
FIG. 2B shows SDS-PAGE analysis of different samples. Lane 1: before SUMO cleavage; Lane 2: after SUMO cleavage; Lane 3: supernatant from centrifugation of the sample after SUMO cleavage reaction; Lane 4: pellet from centrifugation of the sample after SUMO cleavage reaction; Lane 5: flow-through of the Mono S column; Lane 6-1: 4-ml eluted fractions (corresponding to the fractions marked by the two horizontal bars in FIG. 2A).

Samples of different fractions were run on SDS-PAGE (FIG. 2B). Based on the SDS-PAGE results, Fractions 6-10 were pooled (~0.8 mg protein) and were concentrated using 3 kDa Amicon (EMD Millipore).

Figure 3A:
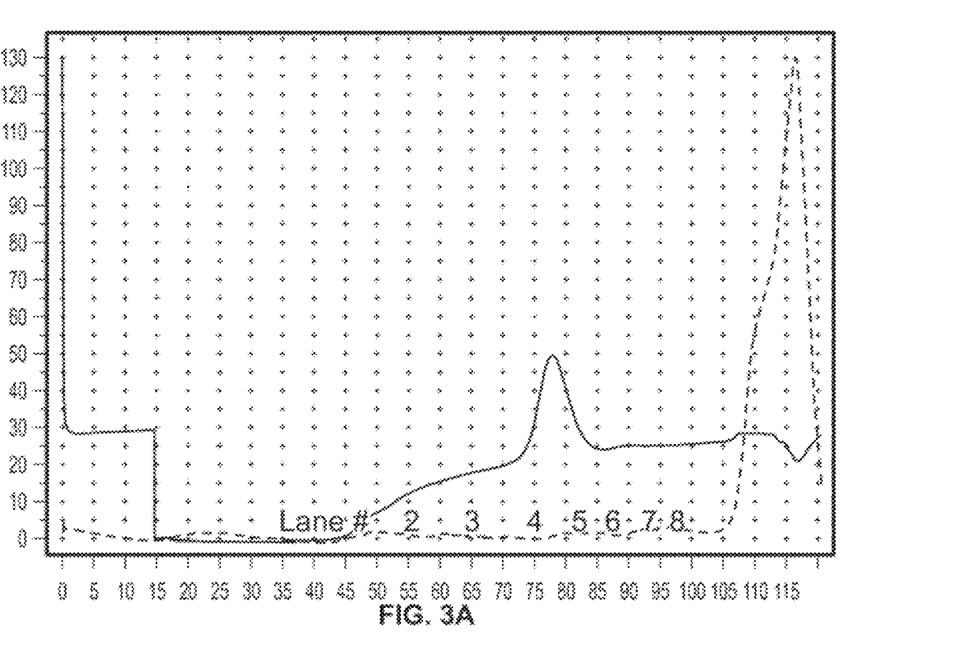
FIG. 3A shows a chromatogram of purification of SUMO-NunDN using the HiLoad SuperDex 75 column (GE Healthcare Life Sciences).
Figure 3B:
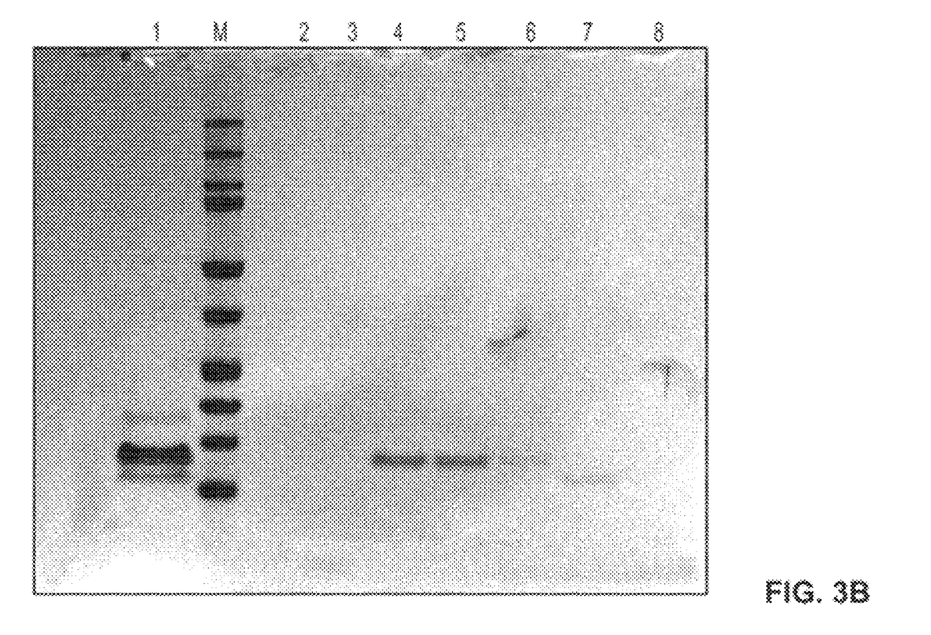
FIG. 3B shows SDS-PAGE analysis of samples of different fractions from the HiLoad SuperDex 75 column. Lane 1: input sample; Lanes 2-8: eluted fractions as indicated in FIG. 3A. Lanes 2-4 correspond to 10-ml fractions; Lanes 5-8 correspond to 5-ml fractions.

The concentrate was injected to the equilibrated HiLoad SuperDex 75 column (GE Healthcare Life Sciences) (FIG. 3A). FIG. 3B shows SDS-PAGE analysis of samples of different fractions from the HiLoad SuperDex 75 column. The purified peptides were >20 mg/mi. 50% glycerol was added to each fraction to obtain a final concentration of 10% glycerol, and the peptides were flash frozen in liquid nitrogen.

Results

Applied to the production of Sumo-NunDN, this technology demonstrated a marked improvement in efficiency as compared with the commercially available BL21(DE3) system. This genetically modified E. coli strain with disrupted ClpP generated at least 10-fold greater protein expression levels (e.g., SUMO-NunDN) than commercial strains such as the BL21(DE3) system, which yields low to moderate levels of the protein. The ability of these genetically modified strains to improve yields of unstable heterologous proteins makes this technology valuable for reducing the associated cost and time needed for protein production.

The scope of the present invention is not limited by what has been specifically shown and described hereinabove. Those skilled in the art will recognize that there are suitable alternatives to the depicted examples of materials, configurations, constructions and dimensions. Numerous references, including patents and various publications, are cited and discussed in the description of this invention. The citation and discussion of such references is provided merely to clarify the description of the present invention and is not an admission that any reference is prior art to the invention described herein. All references cited and discussed in this specification are incorporated herein by reference in their entirety. Variations, modifications and other implementations of what is described herein will occur to those of ordinary skill in the art without departing from the spirit and scope of the invention. While certain embodiments of the present invention have been shown and described, it will be obvious to those skilled in the art that changes and modifications may be made without departing from the spirit and scope of the invention. The matter set forth in the foregoing description and accompanying drawings is offered by way of illustration only and not as a limitation.

The invention claimed is:

1. An engineered bacterium comprising at least one deficient protease, wherein the at least one protease is ClpX, wherein the bacterium is engineered to disrupt ClpX and to express an exogenous polypeptide, wherein, prior to engineering, the bacterium is an *E. coli* that is protease deficient in at least one other protease other than ClpP, and wherein the engineered bacterium overexpresses the polypeptide at a level which is at least 2 fold greater compared to the level of the polypeptide produced by a bacterium not engineered with the deficient protease expressed by said *E. coli* prior to disruption of ClpX, wherein said overexpression is induced at about 37° C.

2. The engineered bacterium of claim 1, wherein the *E. coli* is BL21(D3), wherein the overexpression level is greater than 3 fold, and wherein said overexpressed protein comprises a tag selected from the group consisting of SUMO, c-myc, biotin, polyhistidine and combinations thereof.

3. The engineered bacterium of claim 1, wherein a gene encoding the ClpX protease is knocked out or knocked down in the engineered bacterium.

4. The engineered bacterium of claim 1, wherein a gene encoding the ClpX protease is mutated or deleted in the engineered bacterium.

5. The engineered bacterium of claim 1, further comprising deficient Lon, OmpT, FtsH, or combinations thereof.

6. The engineered bacterium of claim 2, further comprising deficient Lon and deficient OmpT.

7. The engineered bacterium of claim 1, wherein the bacterium comprises a selection marker.

8. The engineered bacterium of claim 7, wherein the selection marker is selected from the group consisting of kanamycin, chloramphenicol, tetracyclin, ampicillin, vancomycin or erythromycin.

9. The engineered bacterium of claim 8, wherein the selection marker is kanamycin.

10. The engineered bacterium of claim 2, wherein the tag is polyhistidine.

11. The engineered bacterium of claim 1, wherein the polypeptide is an antigen, an enzyme, a growth factor, a blood clotting factor, a hormone, or a transcription factor.

12. The engineered bacterium of claim 1, wherein the polypeptide is a heterologous polypeptide.

13. The engineered bacterium of claim 1, wherein the bacterium overexpresses a polypeptide at a level which is at least 5 fold of the level of the polypeptide produced by a bacterium not engineered with the deficient protease.

14. The engineered bacterium of claim 1, wherein the bacterium overexpresses a polypeptide at a level which is at least 8 fold of the level of the polypeptide produced by a bacterium not engineered with the deficient protease.

15. A method for overexpressing a polypeptide, the method comprising the steps of: (a) culturing the engineered bacterium of claim 1 to produce the polypeptide; and (b) isolating the polypeptide.

16. A method for overexpressing a polypeptide in bacteria, the method comprising the steps of: (a) transforming the engineered bacterium of claim 1 with a nucleic acid sequence encoding the polypeptide; (b) culturing the bacterium to produce the polypeptide; and (c) isolating the polypeptide.

* * * * *

SEQUENCE LISTING

<160> NUMBER OF SEQ ID NOS: 1

<210> SEQ ID NO 1
<211> LENGTH: 211
<212> TYPE: PRT
<213> ORGANISM: Artificial Sequence
<220> FEATURE:
<223> OTHER INFORMATION: artificially synthesized

<400> SEQUENCE: 1

```
Met Gly His His His His His His His His Ser Ser Gly His
1               5                   10                  15

Ile Glu Gly Arg His Met Ala Ser Met Ser Asp Ser Glu Val Asn Gln
            20                  25                  30

Glu Ala Lys Pro Glu Val Lys Pro Glu Val Lys Pro Glu Thr His Ile
        35                  40                  45

Asn Leu Lys Val Ser Asp Gly Ser Ser Glu Ile Phe Phe Lys Ile Lys
    50                  55                  60

Lys Thr Thr Pro Leu Arg Arg Leu Met Glu Ala Phe Ala Lys Arg Gln
65                  70                  75                  80

Gly Lys Glu Met Asp Ser Leu Arg Phe Leu Tyr Asp Gly Ile Arg Ile
                85                  90                  95

Gln Ala Asp Gln Thr Pro Glu Asp Leu Asp Met Glu Asp Asn Asp Ile
            100                 105                 110

Ile Glu Ala His Arg Glu Gln Ile Gly Gly Ser Leu Glu Ser Arg Asp
        115                 120                 125

Arg Arg Arg Ile Ala Arg Trp Glu Lys Arg Ile Ala Tyr Ala Leu Lys
130                 135                 140

Asn Gly Val Thr Pro Gly Phe Asn Ala Ile Asp Asp Gly Pro Glu Tyr
145                 150                 155                 160

Lys Ile Asn Glu Asp Pro Met Asp Lys Val Asp Lys Ala Leu Ala Thr
                165                 170                 175

Pro Phe Pro Arg Asp Val Glu Lys Ile Glu Asp Glu Lys Tyr Glu Asp
            180                 185                 190

Val Met His Arg Val Val Asn His Ala His Gln Arg Asn Pro Asn Lys
        195                 200                 205

Lys Trp Ser
    210
```